US009752861B2

(12) United States Patent
Tata et al.

(10) Patent No.: US 9,752,861 B2
(45) Date of Patent: Sep. 5, 2017

(54) FLEXIBLE STRAIN SENSORS

(71) Applicant: Board of Regents, The University of Texas System, Austin, TX (US)

(72) Inventors: Uday Tata, Arlington, TX (US); Smitha Rao, Arlington, TX (US); Jung-Chih Chiao, Grand Prairie, TX (US)

(73) Assignee: The Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 14/438,397

(22) PCT Filed: Oct. 25, 2013

(86) PCT No.: PCT/US2013/066879
§ 371 (c)(1),
(2) Date: Apr. 24, 2015

(87) PCT Pub. No.: WO2014/066802
PCT Pub. Date: May 1, 2014

(65) Prior Publication Data
US 2015/0276372 A1    Oct. 1, 2015

Related U.S. Application Data

(60) Provisional application No. 61/719,115, filed on Oct. 26, 2012.

(51) Int. Cl.
*G01B 7/16* (2006.01)
*A61F 2/16* (2006.01)
(Continued)

(52) U.S. Cl.
CPC ............. *G01B 7/16* (2013.01); *A61F 2/1613* (2013.01); *C23C 14/0605* (2013.01); *C23C 14/35* (2013.01); *C23C 14/5813* (2013.01); *G02C 11/10* (2013.01); *A61F 2/16* (2013.01); *G02C 7/04* (2013.01)

(58) Field of Classification Search
CPC ............. G01B 7/16–7/18; G02C 11/10; A61F 2/1613; C23C 14/0605
See application file for complete search history.

(56) References Cited

U.S. PATENT DOCUMENTS 4,569,738 A * 2/1986 Kieser .................... C03C 17/22
                                                        204/173
4,822,359 A * 4/1989 Tano ..................... A61F 2/1613
                                                        204/192.14
(Continued)

FOREIGN PATENT DOCUMENTS

EP        2233920        9/2010

OTHER PUBLICATIONS

International Search Report and Written Opinion, mailed Feb. 6, 2014.
Yamada, Takeo; Hayamizu, Yuhei; Yamamoto, Yuki; Yomogida, Yoshiki; Izada-Najafabadi, Ali; Futaba, Don N.; and Hata, Kenji, "A Stretchable carbon nanotube strain sensor for human-motion detection", published online Mar. 27, 2011, Nature Nanotechnology, www.nature.com/naturenanotechnology, vol. 6, May 2011.
Tata, Uday; Cao, Hung; Landge, Vaibhav; Nguyen, Cuong M.; and Chiao, J.-C, "Wireless Strain Sensor based on Amorphous Carbon for Human-Motion Detection", IEEE Topical Conference on Biomedical Wireless Technologies, Networks & Sensing Systems, BioWireless'13, IEEE Radio & Wireless Week, Austin, TX Jan. 20-23, 2013.
Peiner, E.; Tibrewala, A.; Bandorf, R.; S.; Luthje, H.; and Doering, L., "Micro Force Sensor with Piezoresistive Amorphous Carbon
(Continued)

*Primary Examiner* — Paul Prebilic
(74) *Attorney, Agent, or Firm* — Thomas | Horstemeyer, LLP

(57) ABSTRACT

In one embodiment, a flexible strain sensor includes a flexible substrate having a top surface and a layer of piezoresistive amorphous carbon formed on the top surface of the substrate.

18 Claims, 9 Drawing Sheets

(51) Int. Cl.
*C23C 14/06* (2006.01)
*C23C 14/35* (2006.01)
*C23C 14/58* (2006.01)
*G02C 11/00* (2006.01)
*G02C 7/04* (2006.01)

(56) References Cited

U.S. PATENT DOCUMENTS

| | | | |
|---|---|---|---|
| 6,096,078 | A | 8/2000 | McDonald |
| 2002/0008340 | A1 | 1/2002 | Behrends |
| 2010/0036288 | A1* | 2/2010 | Lanfermann ...... A41D 13/1281 600/595 |
| 2010/0102403 | A1 | 4/2010 | Celik-Butler |
| 2011/0051322 | A1* | 3/2011 | Pushparaj ............... C23C 16/24 361/525 |
| 2011/0054583 | A1* | 3/2011 | Litt ...................... A61N 5/0601 607/116 |
| 2011/0226066 | A1 | 9/2011 | Anand |
| 2016/0033793 | A1* | 2/2016 | Fenton .................. G02C 11/06 351/158 |

OTHER PUBLICATIONS

Strain Gauge", The 13th International Conference on Solid-State Sensors, Actuators and Mircrosystems, Seoul, Korea, Jun. 5-9, 2005.

Lynch, Jerome P. and Loh, Kenneth J., "A Summary Review of Wireless Sensors and Sensor Networks for Structural Health Monitoring", The Shock and Vibration Digest, vol. 38, No. 2, pp. 91-128 (2006) Sage Publications, Mar. 2006.

Tata, Uday; Nguyen, Cuong M.; Cao, Hung, and Chiao, J.-C, "A Flexible Sputter-Deposited Carbon Strain Sensor", IEEE Sensors Journal, vol. 13, No. 2, Feb. 2013.

\* cited by examiner

FLEXIBLE STRAIN SENSORS

CROSS-REFERENCE TO RELATED APPLICATION(S)

This application is the 35 U.S.C. §371 national stage of, and claims priority to and the benefit of, PCT application PCT/US2013/066879, filed Oct. 25, 2013, which claims priority to and the benefit of U.S. application Ser. No. 61/719,115, filed on Oct. 26, 2012, herein incorporated by reference in their entirety.

BACKGROUND

Strain sensors are used in various applications. In many of these applications, the sensors are used in harsh environments involving high force and low strain. Such sensors are typically formed using rigid materials and are therefore unsuitable for applications in which the object to which the sensor is to be applied has an uneven surface or is flexible. It can therefore be appreciated that it would be desirable to have flexible strain sensors that can conform to uneven surfaces and flex with those surfaces.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have flexible strain sensors that can conform to uneven surfaces and flex with those surfaces. Disclosed herein are examples of such strain sensors. In some embodiments, the strain sensors comprise a flexible substrate on which is formed a layer of piezoresistive amorphous carbon. When the strain sensor is applied to an object, strain can be sensed by measuring changes in the resistance of the amorphous carbon layer.

In the following disclosure, various specific embodiments are described. It is to be understood that those embodiments are example implementations of the disclosed inventions and that alternative embodiments are possible. All such embodiments are intended to fall within the scope of this disclosure.

Recently there has been an increasing interest in developing smart sensors based on polymeric materials capable of reducing the structural restrictions of conventional sensors. Such sensors could be used in the fields of robotics and wearable electronics. Example applications include the measurement of physiological signals, such as breathing, joint movements, and tactile interaction. In such applications, a flexible strain sensor is needed that can conform to non-planar shapes and deform as the surface to which the sensor is applied deforms. Various embodiments of flexible strain sensors are described below.

Figure 1:
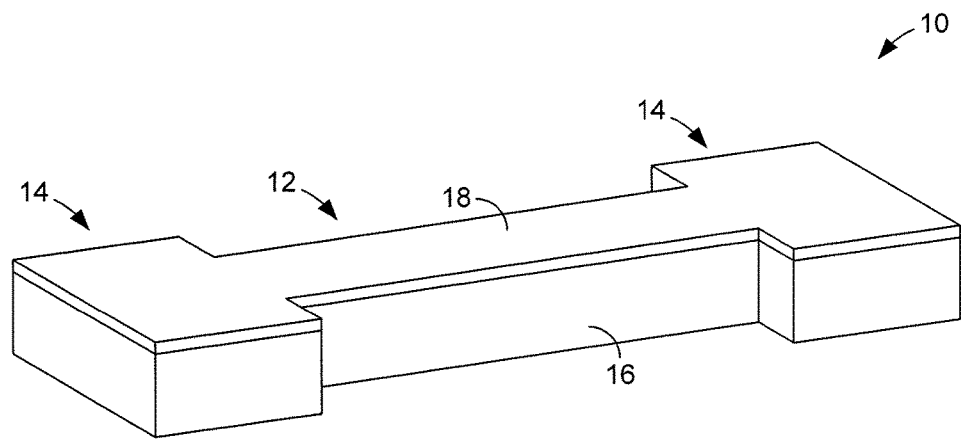
FIG. 1 is a perspective view of a first embodiment of a flexible strain sensor.
Figure 2:
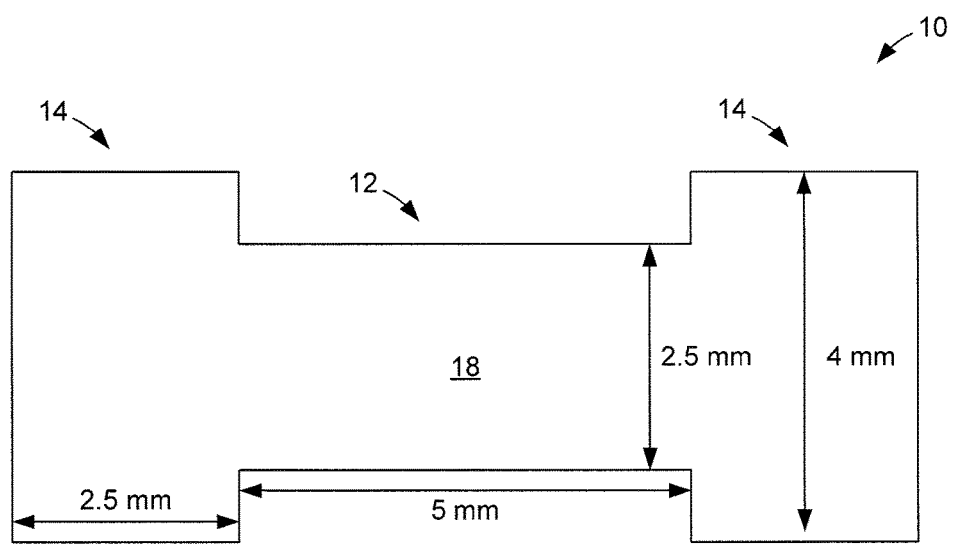
FIG. 2 is a top view of the sensor of FIG. 1.

FIGS. 1 and 2 illustrate a first embodiment of a flexible strain sensor 10. As shown in these figures, the sensor 10 has a general "barbell" shape in which there is an elongated, rectangular central region 12 that is terminated on both ends by relatively wider rectangular end members 14. In this configuration, the central region 12 acts as the active region of the sensor 10 and the end members 14 act as contact pads to which electrical leads (not shown) can attach. Example dimensions for the central region 12 and the ends 14 are illustrated in FIG. 2.

The construction of the flexible strain sensor 10 is most clearly evident from FIG. 1. As shown in that figure, the sensor 10 generally comprises a flexible substrate 16 on which is formed a layer 18 of amorphous carbon. In some embodiments, the substrate 16 is made of a flexible, biocompatible polymeric material. As an example, the substrate 16 can be made of polyimide (e.g., Kapton® by DuPont). Polyimide is a desirable material because of its high flexibility and deformability, biocompatibility, and ease of integration with electronic circuits on a single substrate. Irrespective of the material used, the substrate 16 can be relatively thin. In some embodiments, the substrate 16 is approximately 1 μm to 500 μm thick (e.g., 125 μm thick).

Carbon and its allotropes are useful for strain sensing applications because of their piezoresistive properties. Moreover, the carbon layers can be formed under relatively low-temperature conditions, which enables many different types of materials to be used for the flexible substrate 16. The amorphous carbon layer 18 can be formed on the substrate 16 using substantially any suitable deposition technique. Irrespective of the method used, the carbon layer 18 can be very thin. In some embodiments, the carbon layer 18 is approximately 0.01 μm to 100 μm thick (e.g., 0.5 μm thick).

Figure 3A:
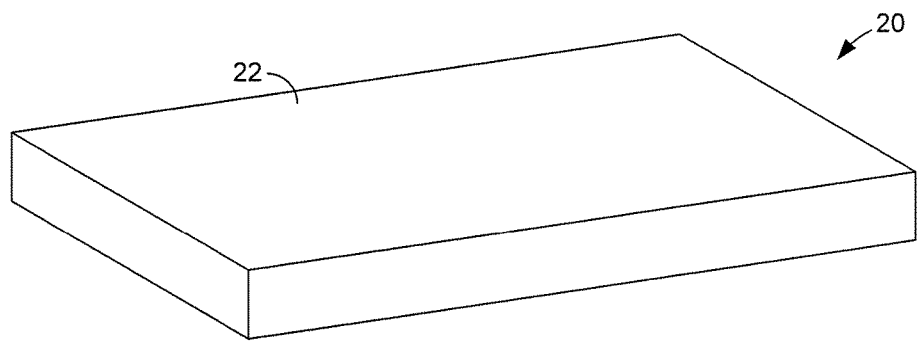
FIG. 3A-3C illustrate steps in an embodiment of a method for fabricating a flexible strain sensor.
Figure 3B:
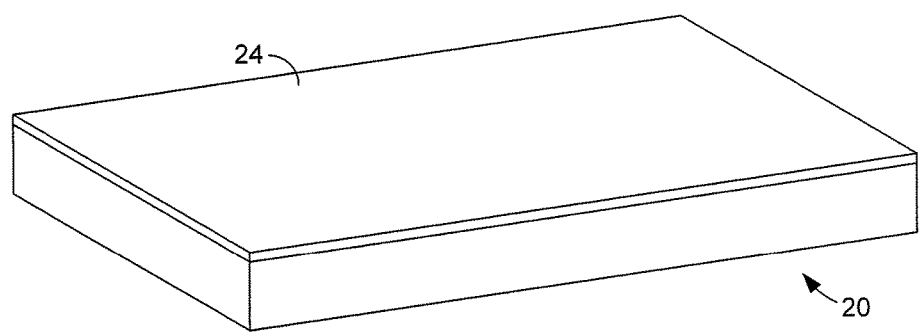
Figure 3C:
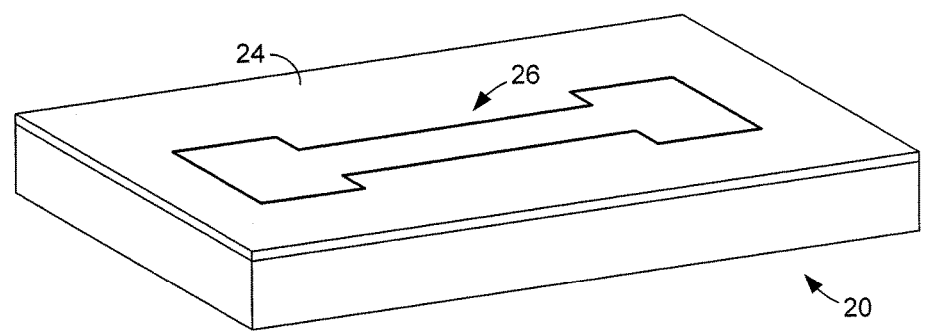

One advantage of the flexible strain sensor 10 is its simplicity and ease of fabrication. FIGS. 3A-3C illustrate steps of an example fabrication method that can be used to form a sensor, such as the sensor 10. Beginning with FIG. 3A, a flexible substrate 20 is formed. In the illustrated example, the substrate 20 is generally rectangular and includes a top surface 22. The substrate 20 can be approximately 1 μm to 500 μm thick. For thin substrates, the substrate can be bonded to a carrier wafer (e.g., silicon wafer) to support the substrate and keep it flat during the fabrication process. Next, as indicated in FIG. 3B, a layer 24 of amorphous carbon is deposited on the top surface 22 of the substrate 20. In some embodiments, the amorphous carbon is deposited using radio frequency (RF) magnetron sputtering at a pressure of approximately 3 mTorr to 5 mTorr and a temperature of approximately 170° C. to 180° C. Finally, with reference to FIG. 3C, the shape of the flexible strain sensor 26 can be obtained by micro-machining the substrate 20 and its amorphous carbon layer 24. In some embodiments, the substrate/layer can be laser micro-machined. In such a case, near vertical wall cuts can be made with great precision. Once the micro-machining has been performed, ultrasonication in acetone and nitrogen air drying can be performed the produce a sensor 26 that is ready for use.

Figure 4:
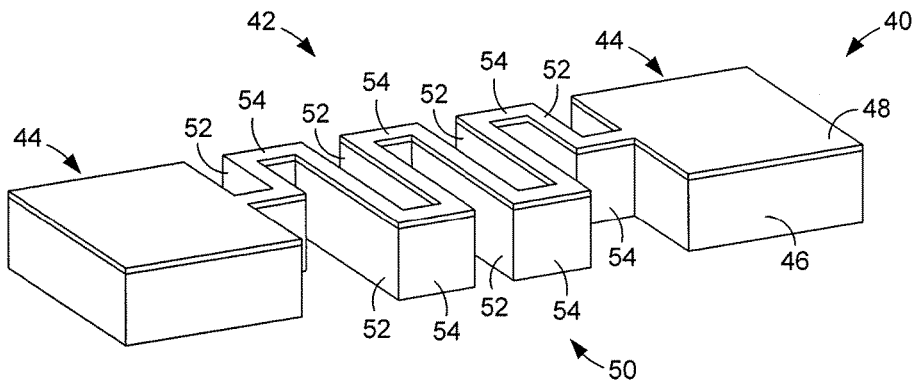
FIG. 4 is a perspective view of a second embodiment of a flexible strain sensor.
Figure 5:
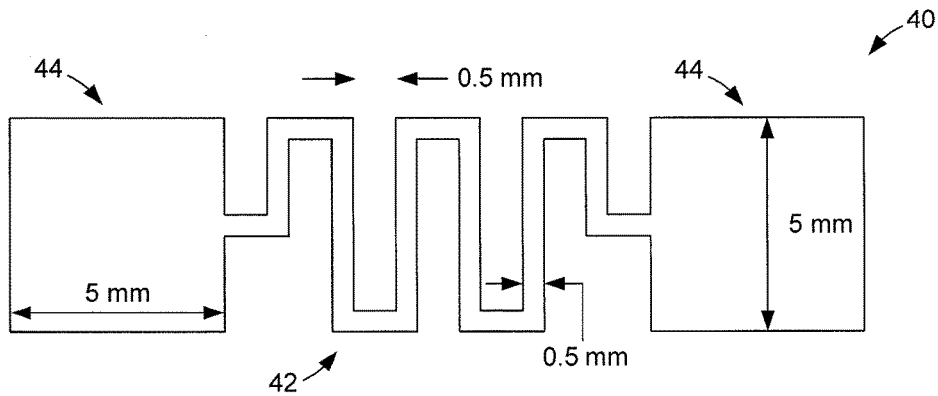
FIG. 5 is a top view of the sensor of FIG. 4.
Figure 6:
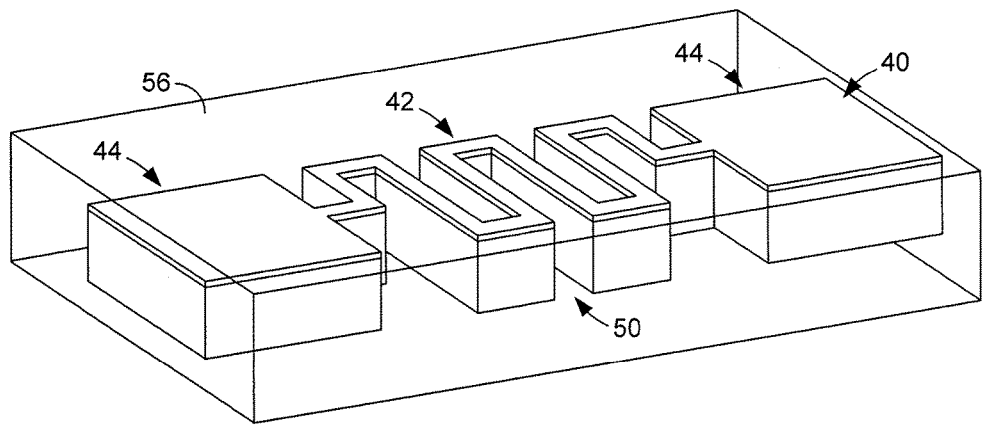
FIG. 6 is a perspective view of the sensor of FIG. 4 shown encapsulated in an elastic polymer.

It is noted that the barbell shape described above is merely exemplary. Indeed, the flexible strain sensor can be formed to have nearly any shape. FIGS. 4 and 5 illustrate one alternative shape. In these figures, a flexible strain sensor 40 comprises an elongated central active region 42 that is terminated by rectangular end members 44. In addition, the sensor 40 also comprises a flexible substrate 46 on which is formed an amorphous carbon layer 48. In this embodiment, however, the active region 42 is not a simple rectangle but instead comprises a continuous, narrow meandered line 50 that comprises multiple parallel lateral segments 52 that are connected to each other at their ends by parallel linear segments 54 that are aligned with a length direction of the sensor 40. In the configuration shown in FIGS. 4 and 5, the lateral segments 52 are perpendicular to the linear segments 54 and the length direction of the sensor 40. With such a configuration, the sensor 40 is capable of stretching along it length direction with an object with which it is used so as to withstand higher strains. FIG. 5 shows example dimensions for the sensor 40. As shown in FIG. 6, the flexible strain sensor 40 can, in some embodiments, be embedded in an elastic material 56, such as polydimethlysiloxane (PDMS), to increase the sensor's ability to stretch. In some embodiments, the sensor 40 can elongate to approximately 125% of its initial length.

A flexible strain sensor having a configuration similar to that shown in FIG. 6 was fabricated for testing purposes. The width and length of the active region was 0.5 mm and 10 mm, respectively, and the sensor had the meandered shape shown in FIGS. 4-6. A 0.5 µm thick amorphous carbon film was deposited on a 125 µm thick polyimide film by RF magnetron sputtering from a graphite target using a custom-designed sputter system at 150 W power for a period of 8 hours. The chamber pressure was maintained at 3 to 5 mTorr and the substrate temperature for the process was kept below 200° C.

Copper connection wires were attached to the contact pads of the flexible strain sensor with conductive epoxy. The sensor was then embedded into PDMS in a strip shape, as shown in FIG. 6. The overall dimensions of the sensor were 20×5×0.125 mm³. The initial resistance for the fabricated sensor was measured at the zero-strain state with values in the range of 11-13 kΩ.

Figure 7:
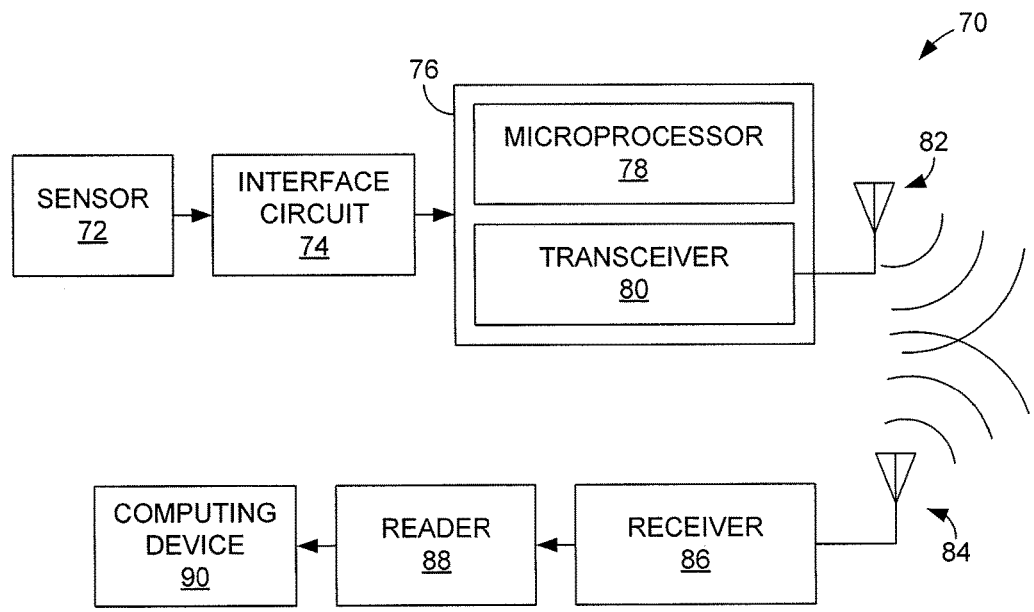
FIG. 7 is a block diagram of an embodiment of a wireless sensing system that incorporates a flexible strain sensor.

In some applications, wireless sensing of strain is desirable. Therefore, a wireless sensing system was designed for testing purposes. FIG. 7 shows the major components of the wireless sensing system 70. As depicted in this figure, the system 70 comprised a flexible strain sensor 72, and interface circuit 74, a controller 76 that includes a microprocessor 78 and a first transceiver 80, and a first antenna 82. In addition, apparatus was setup to receive data from the system 70, including a second antenna 84, a second transceiver 86, a reader 88, and a computing device 90. In use, the sensor 72, which could be connected to or implanted within a body, senses motion as a strain and a corresponding signal is fed to the interface circuit 74. The interface circuit 74 converts this signal into a format that is suitable for the microprocessor 78. The microprocessor 78 processes the signals and digital data packets are then wirelessly transmitted by the first transceiver 80 and the first antenna 82. The packets are received by the second antenna 84 and the second transceiver 86, are read by the reader 88, and then can be presented on the computing device 90. In some embodiments, the packets can be transmitted using a standard RF network protocol with a wireless communication range of up to 35 m in normal situations.

Figure 8:
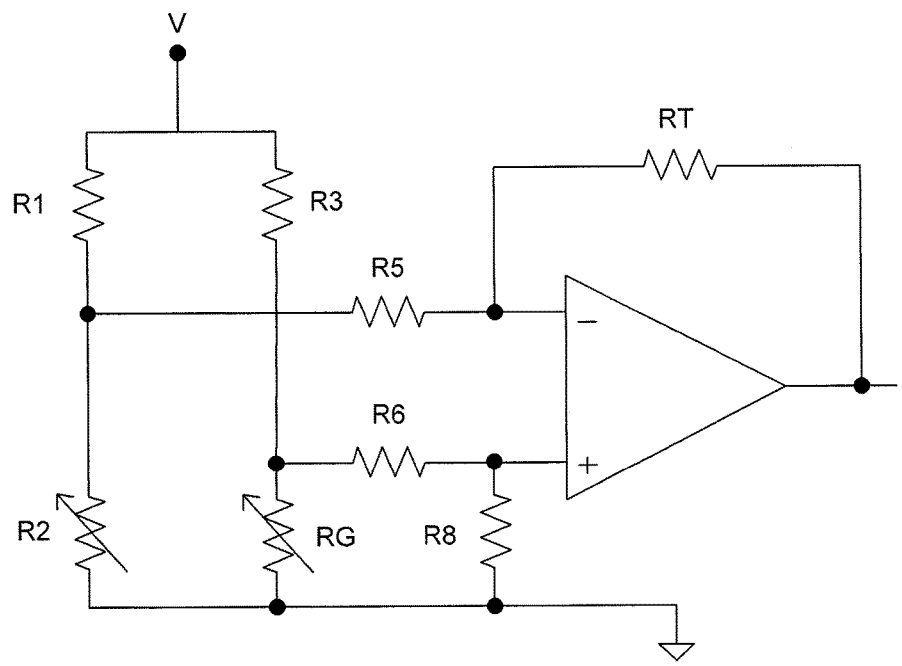
FIG. 8 is a circuit diagram of a circuit that was used to test a flexible strain sensor.

The strain sensor was connected in a Wheatstone bridge circuit configuration as shown in FIG. 8. RG was the gauge resistance, initially 11.29 kΩ. R1 and R3 were approximately 11 kΩ. The bridge was balanced using a variable resistor R2. The output voltage of the bridge at the zero strain can be calculated as $$V_{BRG0} = V\left(\frac{R_G}{R_3 + R_G} - \frac{R_2}{R_1 + R_2}\right) \tag{1}$$

The output of the bridge was fed to a differential amplifier. The resistors R5, R6, R7, and R8 were 11, 11, 110, and 110 kΩ, respectively. The ratio of R7 to R5 determined a gain of 10. The output of the differential amplifier at zero strain can be calculated as $$V_{DIFF0} = V\frac{-R_7}{R_5}\left(\frac{R_G}{R_3 + R_G} - \frac{R_2}{R_1 + R_2}\right) \tag{2}$$

Figure 9:
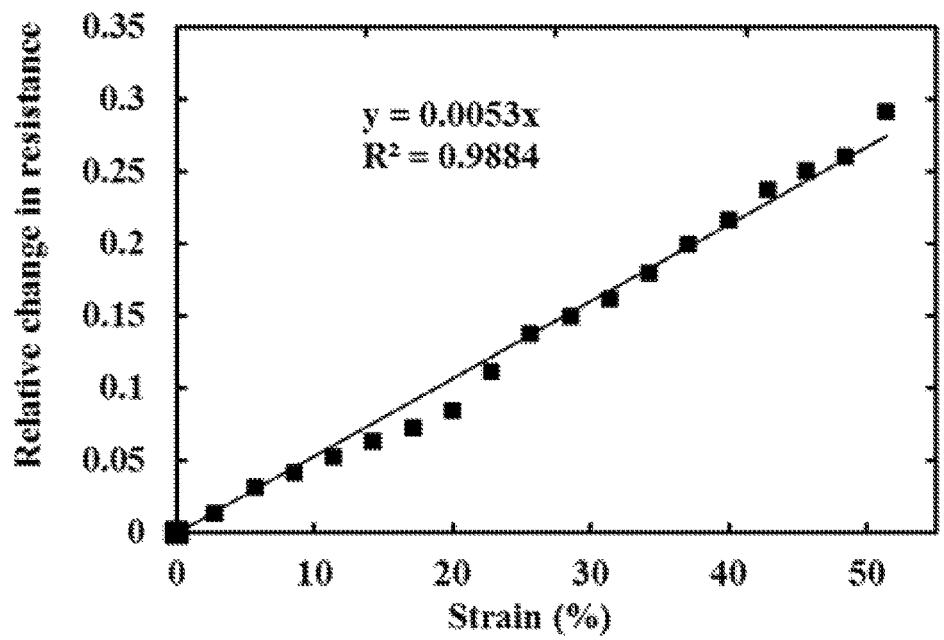
FIG. 9 is a graph that shows the sensitivity of a flexible strain sensor that was tested.

The strain sensor was calibrated using two stages with one fixed and the other one spring loaded for translational motion. A tensile load was applied to the sensor by traversing the translational stage using a lead screw. For each loading, the corresponding strain value was calculated. A charged-coupled device (CCD) camera assembled with a microscopic objective of 10× magnification was used to monitor the deformation of strain sensor under loading. The translational stage was traversed in 20 discrete steps with 200 µm each up to 2 mm. The corresponding strains were in the range of 0 to 51% in an increment of 2.8% strain. The relative change in resistance as a function of strain is shown in FIG. 9. The slope of the curve indicates a gauge factor, or sensitivity, of 0.534. The measured gauge factor was relatively small over a large strain range as it was contributed to by both the sensing film and the meander line structure.

Figure 10:
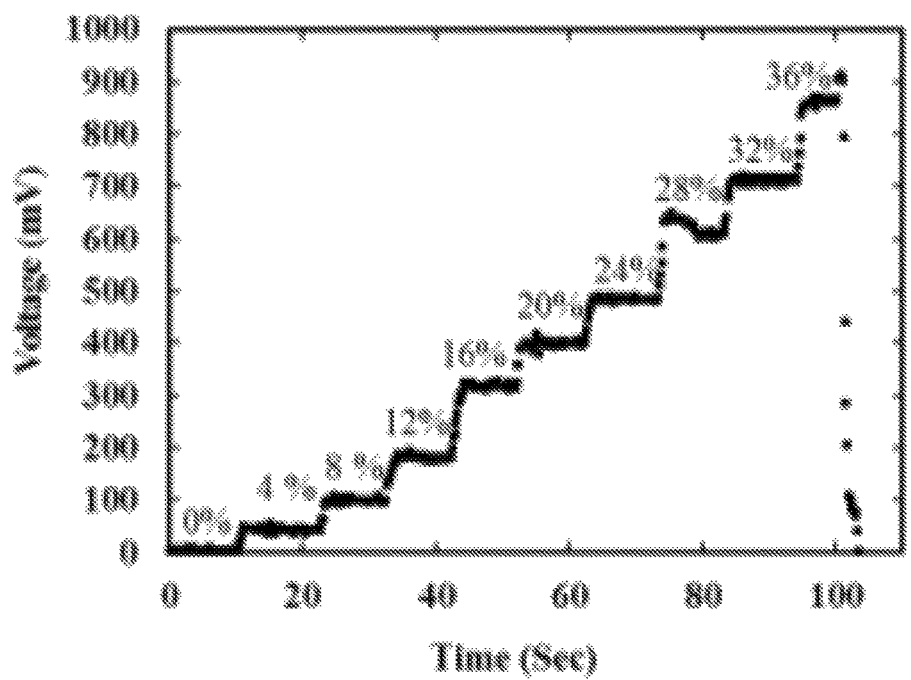
FIG. 10 is a graph of output signals obtained via wireless communication from a flexible strain sensor that was tested.

The strain sensor was interfaced to the wireless module and strains were applied using a mechanical setup. The sensor signals were converted and processed into digital format before being wirelessly transmitted to the receiver. After demodulation, output voltage was recorded and displayed in the computing device at a sampling rate of 10 samples/sec. FIG. 10 shows the measured results for different strains with an increment of 4% strain. The fluctuation in the sensor reading at any particular strain was found to be less than 1.4%, which indicates good stability. It should be noted that the fluctuation included all noise and interference sources throughout the wireless communication. FIG. 10 also shows the calibration relationship between wireless output and applied strain. The sensitivity was found to be 24.15 mV/strain (%).

The sensor was then mounted on a subject's knee joint when in a resting position and was secured with belts. A wearable communication module was attached on the belt above the knee. The wearable module weighed 4 g with dimensions of 3×1.5×0.2 $cm^3$ and did not limit the subject's mobility.

Figure 11:
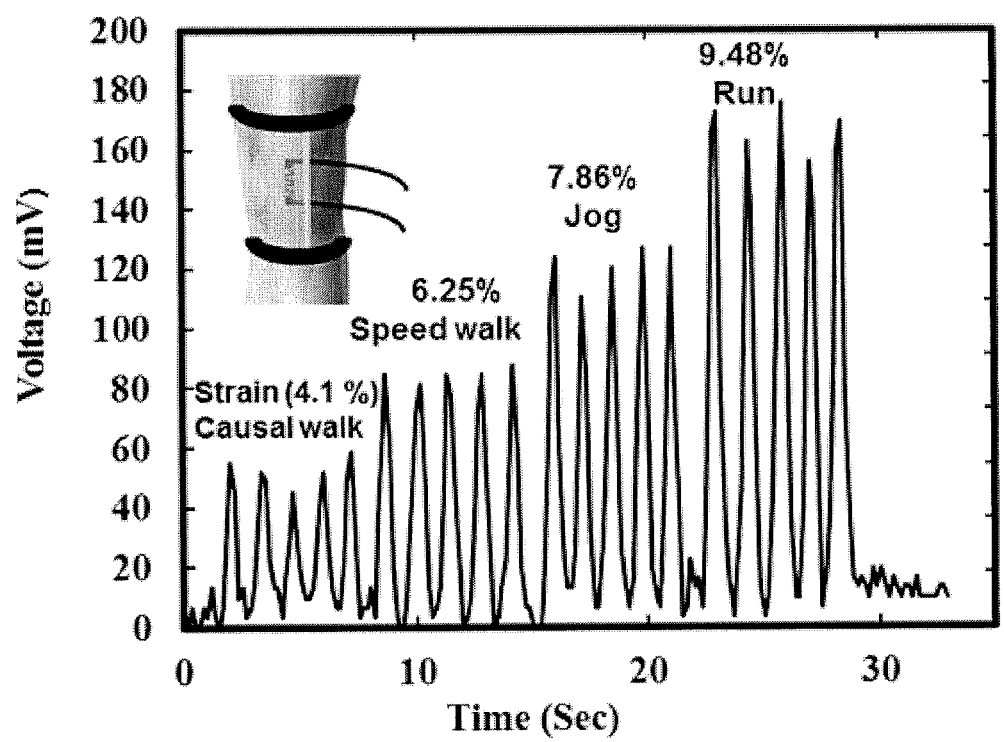
FIG. 11 is a graph of dynamic responses of a flexible strain sensor that was tested.

The knee joint flexed when the subject was in motion. The magnitude of the flexing depended on the types of motion. Due to the flexing of the knee joint, the sensor experienced strains across the joint area. Four different types of human motion, including casual walking, speed walking, jogging, and running, were performed. Each motion was repeated 5 times at a 1-Hz frequency. The results that were wirelessly received at the computing device are shown in FIG. 11. With the calibration curve, strain values experienced by the knee joint were found to be 4.1%, 6.25%, 7.86%, and 9.48% at casual walking, speed walking, jogging, and running, respectively. The dynamic response time for the sensor was found to be within 400 ms, which included the strain sensor response time, signal processing time in the wearable module, wireless communication time, and computing device processing time. Results also indicated reasonable repeatability in the sensor responses.

Figure 12:
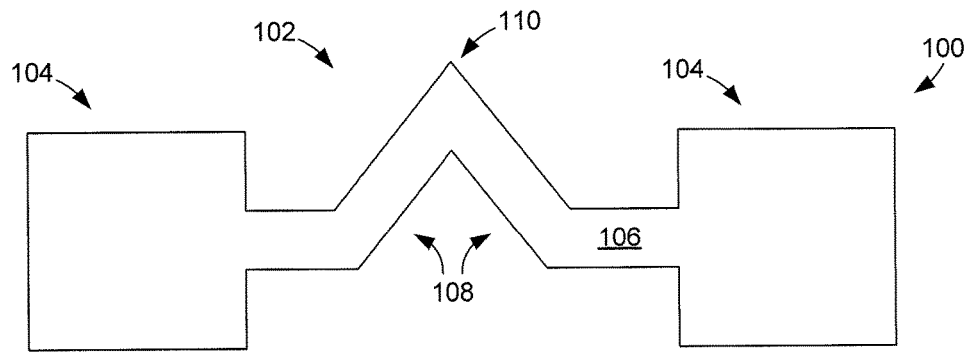
FIG. 12 is a top view of a third embodiment of a flexible strain sensor.
Figure 13:
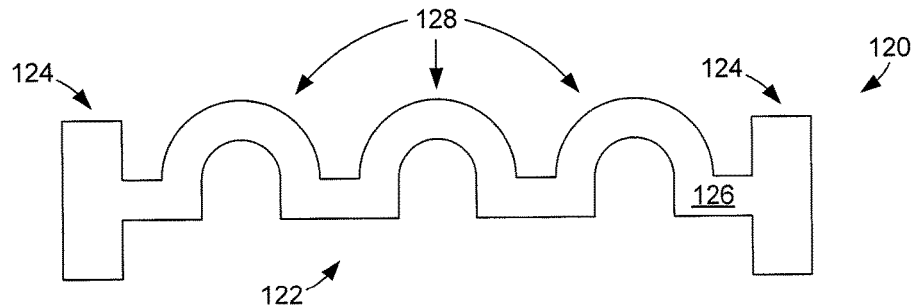
FIG. 13 is a top view of a fourth embodiment of a flexible strain sensor.
Figure 14:
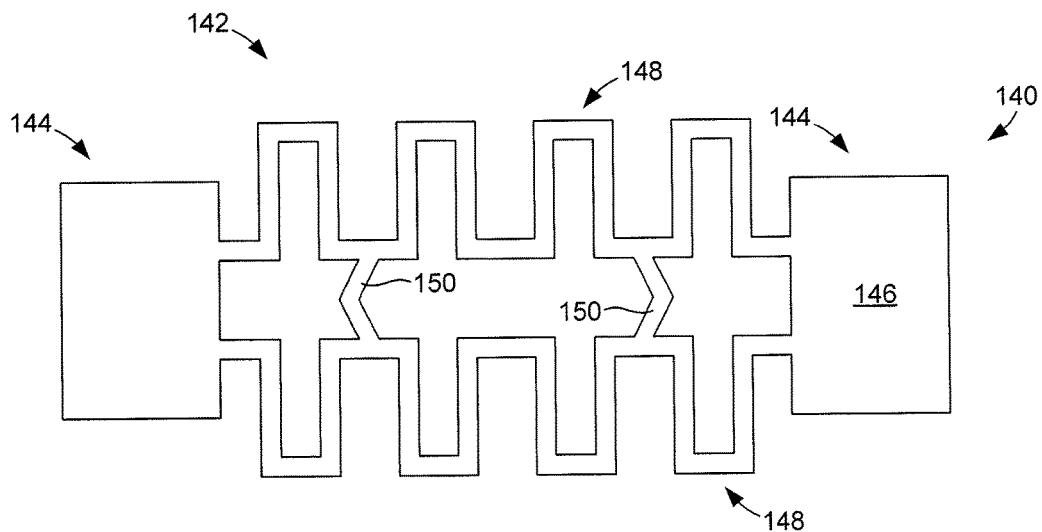
FIG. 14 is a top view of a fifth embodiment of a flexible strain sensor.

FIGS. 12-14 show further embodiments of flexible strain sensors. Beginning with FIG. 12, a flexible strain sensor 100 comprises an elongated central active region 102 that is terminated by rectangular end members 104. The sensor 100 comprises a flexible substrate (not visible) on which is formed an amorphous carbon layer 106. In this embodiment, the active region 102 comprises a continuous line that forms two diagonal segments 108 that together form a chevron shape that forms a point 110.

Referring next to FIG. 13, a flexible strain sensor 120 comprises an elongated central active region 122 that is terminated by rectangular end members 124. The sensor 120 also comprises a flexible substrate (not visible) on which is formed an amorphous carbon layer 126. In this embodiment, however, the active region 122 comprises a continuous line that includes three semicircular loops 128.

With reference to FIG. 14, illustrated is a flexible strain sensor 140 that comprises an elongated central active region 142 that is terminated by rectangular end members 144. The sensor 120 also comprises a flexible substrate (not visible) on which is formed an amorphous carbon layer 146. In this embodiment, the active region 142 comprises two continuous meandered lines 148 that each comprise multiple parallel lateral segments that are connected to each other at their ends by parallel linear segments that are aligned with a length direction of the sensor 148, in similar manner to the meandered line 50 described above. In addition, the active region 142 includes two lateral segments 150 positioned between the meandered lines 148 that join the lines together. In the illustrated example, the lateral segments 150 each have a chevron shape similar to that described above in relation to the sensor 100 shown in FIG. 12. Although the embodiment of FIG. 14 is similar to that shown in FIGS. 4-6, the embodiment of FIG. 14 is more balanced and therefore is less likely to twist when stretched.

Figure 15:
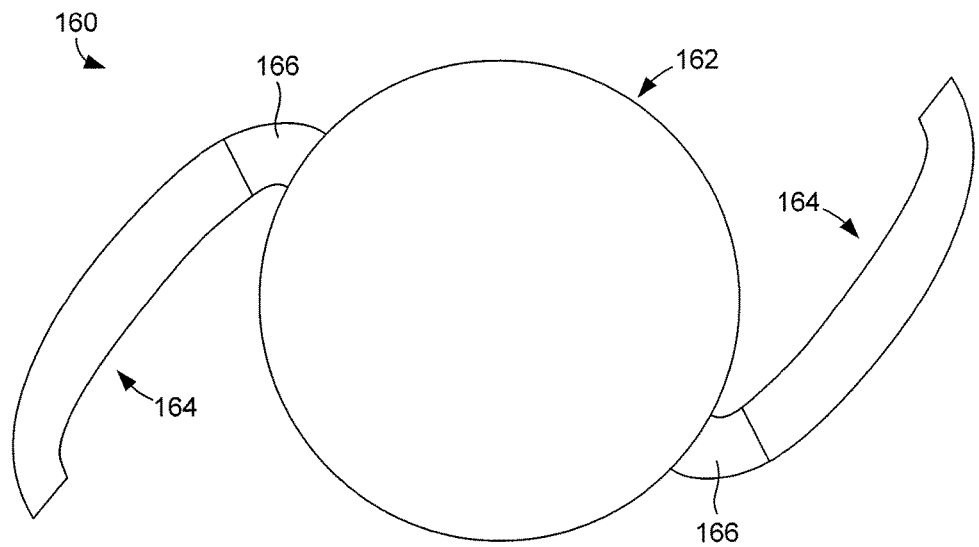
FIG. 15 is a top view of a first intraocular lens that incorporates flexible strain sensors.

The flexible strain sensors can be used in many different applications, including medical applications. One particularly interesting application is incorporation of the sensors into an implantable intraocular lens (IOL). FIG. 15 shows an example IOL 160 to which sensors have been applied. As shown in this figure, the IOL 160 comprises a generally circular central body 162 through which a patient sees when the IOL has been implanted and asymmetric, curved elongated arms 164 that extend outward from the body that stabilize the IOL within the eye. The body 162 and arms 164 can be made from a continuous substrate of flexible, biocompatible polymeric material, such as PDMS, polyimide, liquid crystal polymer, or parylene-c. As is further shown in FIG. 15, strain sensors 166 that comprise patches of piezoresistive amorphous carbon have been directly deposited on the arms 164 near the points at which they attach to the body 162 for the purpose of measuring strain within the IOL 160. By connecting electrical conductors to opposite ends of each patch, strain in those areas can be determined.

Figure 16:
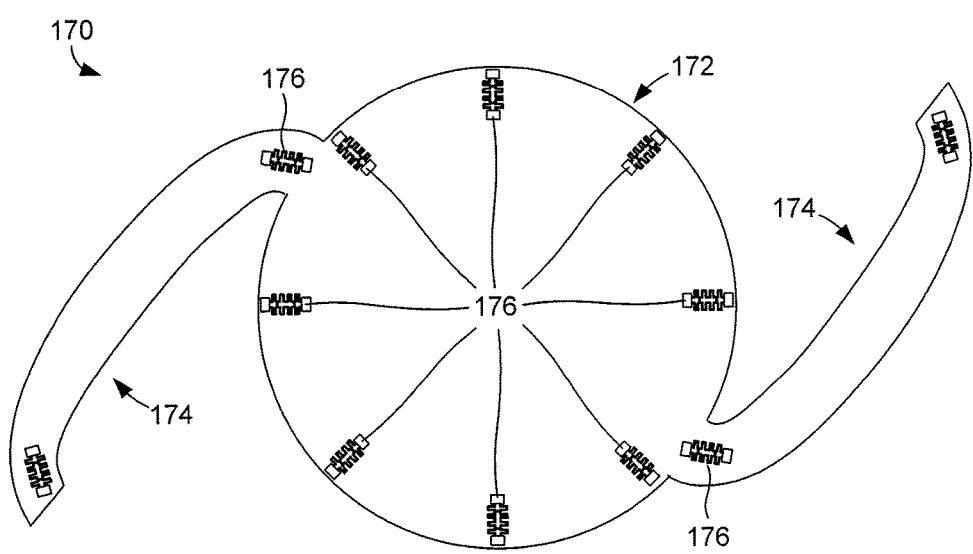
FIG. 16 is a top view of a second intraocular lens that incorporates flexible strain sensors.

FIG. 16 shows a further implantable IOL 170 to which sensors have been applied. As shown in this figure, the IOL 170 also comprises a generally circular central body 172 and asymmetric, curved elongated arms 174 that extend outward from the body. In this embodiment, however, multiple flexible strain sensors 176 have been formed on the IOL 172, both on its body 172 and its arms 174. As above, each sensor 176 is formed by depositing piezoresistive amorphous carbon on the IOL. In this case, however, each sensor 176 has a configuration similar to that shown in FIG. 14.

Figure 17:
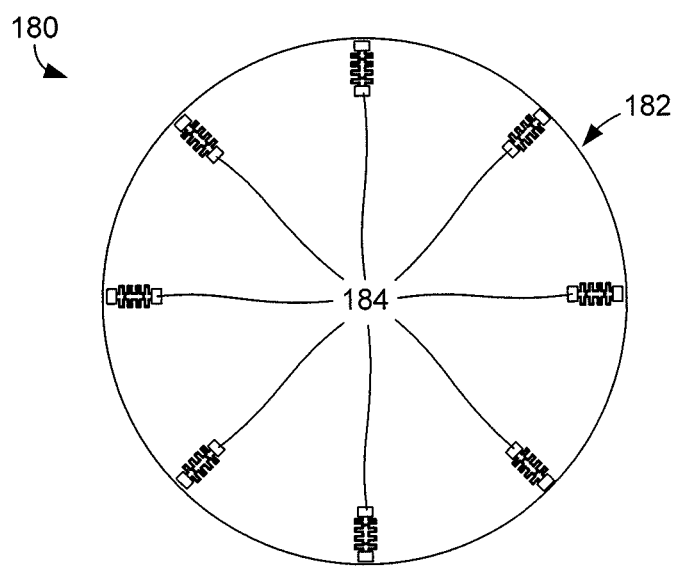
FIG. 17 is a top view of a contact lens that incorporates flexible strain sensors.

FIG. 17 shows a contact lens 180 having a generally circular body 182 on which are multiple flexible strain sensors 184, each also having a configuration similar to that shown in FIG. 14.

The invention claimed is:

1. A flexible strain sensor comprising:
a flexible polymeric substrate having a top surface; and
a layer of amorphous carbon formed on the top surface of the substrate;
wherein the sensor comprises a meandered active region formed by the substrate and the layer of amorphous carbon, the substrate and the layer of amorphous carbon both tracing a meandered line within the active region.

2. The sensor of claim 1, wherein the substrate is biocompatible.

3. The sensor of claim 1, wherein the substrate is a polyimide substrate.

4. The sensor of claim 1, where in the substrate is approximately 1 μm to 500 μm thick.

5. The sensor of claim 1, wherein the amorphous carbon layer is approximately 0.01 μm to 100 μm thick.

6. The sensor of claim 1, wherein the sensor further comprises end members provided at ends of the active region.

7. The sensor of claim 6, wherein the active region comprises multiple parallel meandered lines.

8. The sensor of claim 7, wherein the active region further comprises lateral segments that join the meandered lines.

9. An optical device comprising:
a lens body; and
a flexible strain sensor provided on the lens body, the sensor including a flexible polymeric substrate having a top surface and a layer of amorphous carbon formed on the top surface of the substrate, wherein the sensor comprises a meandered active region formed by the substrate and the layer of amorphous carbon, the substrate and the layer of amorphous carbon both tracing a meandered line within the active region.

10. The device of claim 9, wherein the device is an implantable intraocular lens.

11. The device of claim 10, wherein the implantable intraocular lens further comprises arms that extend from the body and wherein a strain sensor is provided on each arm.

12. The device of claim 10, wherein the implantable intraocular lens comprises a body and wherein a strain sensor is provided at each of multiple positions around the periphery of the body.

13. The device of claim 9, wherein the device is a contact lens.

14. The device of claim 13, wherein contact lens comprises a body and wherein a strain sensor is provided at each of multiple positions around the periphery of the body.

15. The sensor of claim 1, wherein the meandered line comprises multiple parallel lateral segments and multiple parallel linear segments.

16. The sensor of claim 1, wherein sensor is embedded in an elastic material.

17. The device of claim 9, wherein the meandered line comprises multiple parallel lateral segments and multiple parallel linear segments.

18. The device of claim 9, wherein sensor is embedded in an elastic material.

* * * * *